(12) United States Patent
Gattuso et al.

(10) Patent No.: US 7,410,363 B1
(45) Date of Patent: Aug. 12, 2008

(54) ELECTRICAL CONNECTOR HAVING COMPLIANT BIASING DEVICE

(75) Inventors: Andrew Gattuso, Chandler, AZ (US); Shih-Wei Hsiao, Tu-cheng (TW); Chun-Fu Lin, Tu-cheng (TW)

(73) Assignee: Hon Hai Precision Ind. Co., Ltd., Taipei Hsien (TW)

( * ) Notice: Subject to any disclaimer, the term of this patent is extended or adjusted under 35 U.S.C. 154(b) by 0 days.

(21) Appl. No.: 12/001,687

(22) Filed: Dec. 12, 2007

(51) Int. Cl.
*H01R 12/00* (2006.01)

(52) U.S. Cl. ......................................... 439/71; 439/526
(58) Field of Classification Search ............. 439/70–73, 439/330, 331, 374, 525
See application file for complete search history.

(56) References Cited

U.S. PATENT DOCUMENTS 5,073,116 A * 12/1991 Beck, Jr. ..................... 439/71
5,290,193 A * 3/1994 Goff et al. .................... 439/331
5,342,205 A * 8/1994 Hashiguchi ................... 439/66
6,644,981 B2 * 11/2003 Choy ........................... 439/70

\* cited by examiner

*Primary Examiner*—Tho D Ta
(74) *Attorney, Agent, or Firm*—Wei Te Chung

(57) ABSTRACT

An electrical connector comprising: an insulative housing defining a top surface with a plurality contact terminals planted within the housing; a frame having an rectangle framework securely attaching to the housing defining sidewalls jointly formed a room for receiving an IC package therein, engaging hollows are defined at an pair of opposite corner of the framework and a chamber at a corner of the framework; a compliant biasing device positioned in the said chamber of the corner of framework for positioning the IC package; a thermal control element having alignment pins related to the engaging hollows, said thermal control element pushing the compliant biasing device sliding in the chamber so the compliant biasing device attaching on the IC package to ensure proper and reliable electrical interconnection.

10 Claims, 6 Drawing Sheets

ELECTRICAL CONNECTOR HAVING COMPLIANT BIASING DEVICE

BACKGROUND OF THE INVENTION

1. Field of the Invention

The present invention relates to the art of electrical connectors, and more particularly to an electrical connector provided with an advanced package compliant biasing device for positioning a package received in an insulative housing of the electrical connector.

The present invention relates to an electrical connector, and more particularly, to a LGA/LGA electrical connector having compliant biasing device such that when an IC device is seated onto the electrical connector, the compliant biasing device will drive the IC device diagonally against two datum planes so as to ensure proper and reliable electrical interconnection therebetween.

2. Description of the Related Art

U.S. Pat. No. 6,164,980 issued to Goodwin on Dec. 20, 2000 describes a connector electrical in which the present invention is related. According to Goodwin, an integrated circuit alignment feature facilitates alignment of an integrated circuit chip relative to an electrical, and a electrical alignment feature facilitates alignment of the electrical relative to a printed circuit board. The electrical includes four walls that define a rectangular frame in which the integrated circuit chip is mounted. A first alignment contact point extends inward relative to a first one of the walls. Second and third alignment contact points extend inward from a second one of the walls, which adjoins the first wall. A first force is applied against the integrated circuit chip from a third one of the walls, which is parallel with the first wall. Second and third forces are applied against the integrated circuit chip from a fourth one of the walls, which is parallel with the second wall. Hence, the integrated circuit chip is aligned in a corner defined by the first and second walls, and is oriented by the three alignment contact points. Spring members may be employed to provide the first, second and third forces. The Goodwin electrical connector is generally referred to as LGA/LGA electrical connector in which the contact terminals each features a spring arm directly contact to an IC device and a printed circuit board.

U.S. Pat. No. 6,908,316 issued to Ma on Jun. 21, 2005 discloses another type of electrical connector. According to Ma, an electrical connector in accordance with a first embodiment of the present invention comprises an insulative base mounted on a printed circuit board, a metal clip pivotably engaged on the base, and a lever for fastening the clip onto the base. The base is substantially rectangular. A floor is defined in a middle of the base. A rectangular raised support area is provided around a periphery of the floor. The support area defines four inner sidewalls. The sidewalls and the floor cooperatively define a substantially rectangular cavity therebetween. One of the sidewalls defines a pair of protrusions with inner surface extending into the cavity, wherein the inner surfaces of the two protrusions are parallel to the sidewall, and are coplanar with each other. The other three sidewalls each define a single protrusion extending perpendicularly therefrom.

U.S. patent application Ser. No. 11/708,720 filed under David Gregory Howell on Sep. 4, 2007 entitled LAND GRID ARRAY CONNECTOR WITH REINFORCEMENT STIFFENER disclosed an electrical connector pertinent to the current invention.

From the above description of prior art, it can be readily understood that in this LGA/LGA electrical connector, generally there are two adjacent sidewalls are used a datum plane in which all interconnecting points between an IC device and the contact terminals are referred. On the other hand, in order to ensure the IC device is correctly seated onto their intended position, another two side walls, which are normally opposite to the datum plane, are each provided with a push finger, such as elements 34, 36, 38 and 40 as described in FIG. 2 of Goodwin.

However, improvement is also required and necessary in order to provide better and more reliable function of the electrical connector.

SUMMARY OF THE INVENTION

It is an object of the current invention to provide an electrical connector having compliant biasing device such that when an IC device is seated onto the electrical connector, the compliant biasing device will drive the IC device diagonally against two datum planes so as to ensure proper and reliable electrical interconnection therebetween.

To fulfill the above-mentioned objects, an electrical connector accordance with a preferred embodiment comprises an insulative housing, a number of terminals embedded in the housing in an array manner, a frame attached on the housing, a thermal control element mounted on the frame, an advanced package compliant biasing device and a clapboard. The frame having an rectangle framework securely attaching to the housing defining sidewalls jointly formed a room for receiving an IC package therein, engaging hollows are defined at an pair of opposite corner of the framework and a chamber at a corner of the framework. The compliant biasing device positioned in the said chamber of the corner of framework for positioning the IC package. The thermal control element having alignment pins correspond to the engaging hollows. The thermal control element drives the compliant biasing device sliding in the chamber so the compliant biasing device attaching on the IC package to ensure proper and reliable electrical interconnection therebetween.

Other features and advantages of the present invention will become more apparent to those skilled in the art upon examination of the following drawings and detailed description of preferred embodiments, in which:

DETAILED DESCRIPTION OF PREFERRED EMBODIMENT

Figure 1:
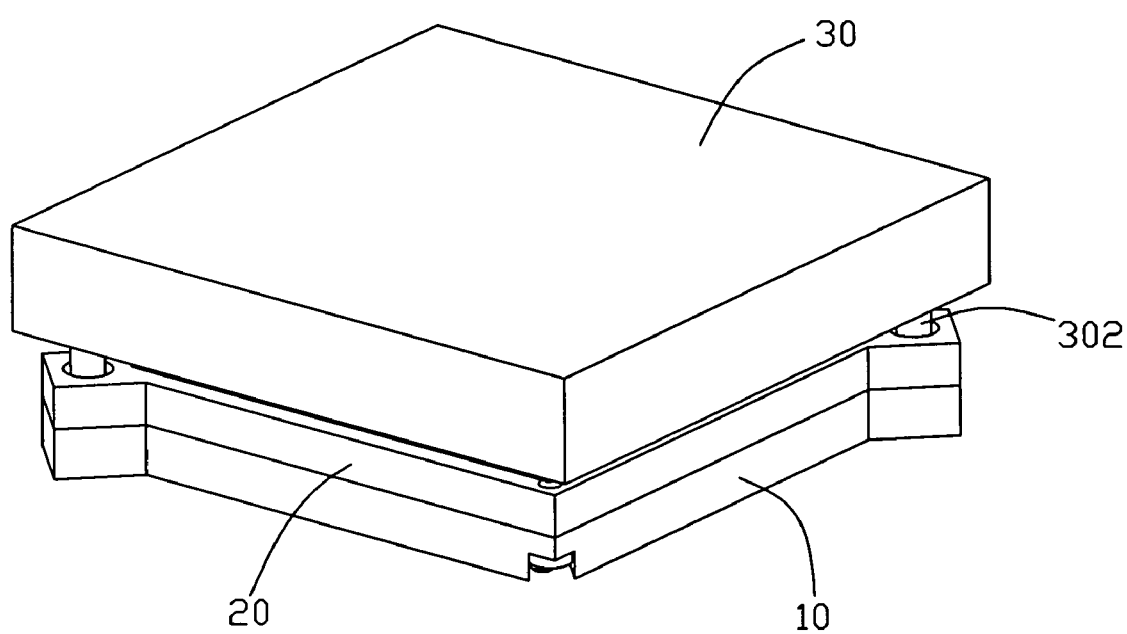
FIG. 1 is an assemble, perspective view of an electrical connector according to a preferred embodiment of the present invention.
Figure 2:
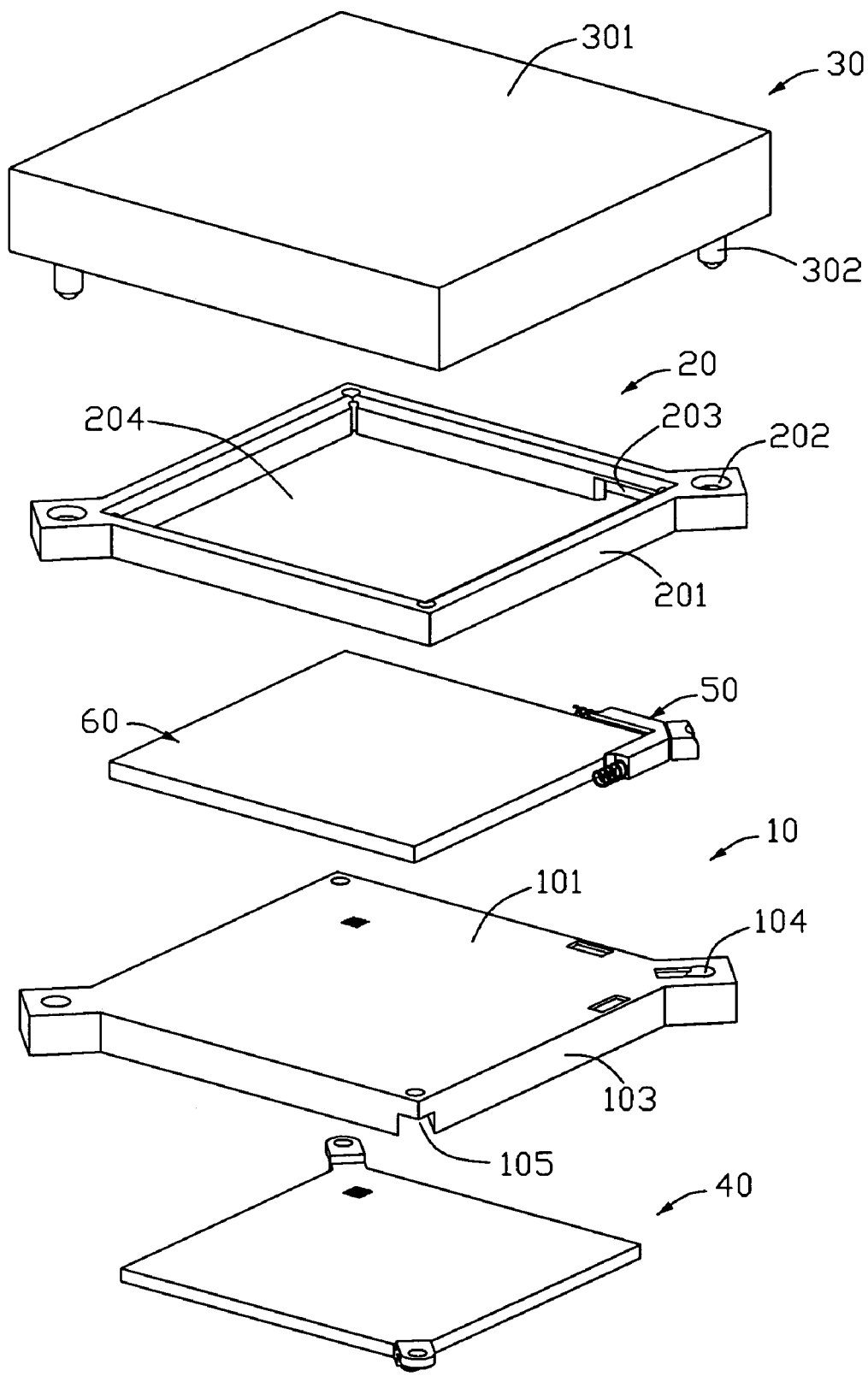
FIG. 2 is an exploded, perspective view of an electrical connector according to a preferred embodiment of the present invention.
Figure 3:
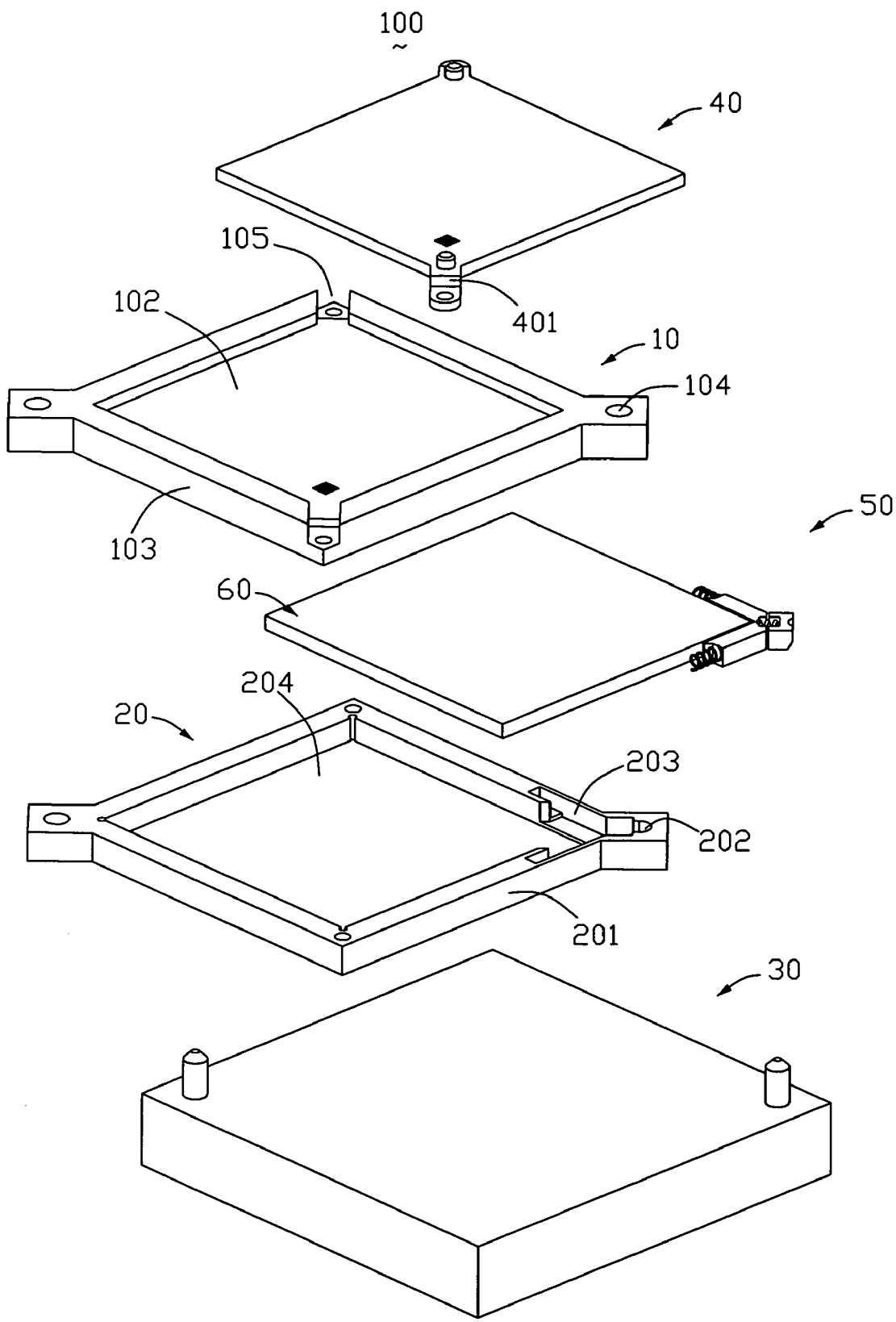
FIG. 3 is another perspective view of the electrical connector of FIG. 2.

Referring to FIGS. 1 to 3, an electrical connector in accordance with the preferred embodiment of the present invention. The electrical connector comprises an insulative housing 10, a plurality of terminals planted in the housing (not shown), a frame 20 mounted on the housing, a thermal control element 30 engaged with the housing 10 and the frame 20, a clapboard 40 a compliant biasing device 50.

The insulative housing 10 has top surface 101 for receiving the IC package 60 and a bottom surface 102, sidewalls 103 extending perpendicularly from the bottom surface 102 and jointly define a cavity (not labeled) for receiving the clapboard 40. A pair of engaging holes 104 is formed at the opposite corner of the housing 10 for engaging with the thermal control element 30, at the other pair corners forms a pair of grooves 105 for mounting with the clapboard 40.

The frame 20 defines a generally rectangle framework 201. A pair of engaging hollows 202 defined in the framework related to the engaging holes 104 for engaging with thermal control element 30. A generally Y-shaped chamber 203 is formed at the corner of the bottom of the frame extending through one of the engaging hollows 202. The frame 20 mounted on the housing 10 defines a room 204 for receiving IC package 60.

The thermal control element 40 has a base 301 of generally rectangular configuration and a pair of alignment pins 302 formed at the opposite corner of the base. The alignment pins 302 are generally shaped in column with the distal end in a trochiformis shape. In assembly, said alignment pins can insert into the engaging holes 104 and engaging hollows 202.

The compliant biasing device 50 includes a first driving portion comprising a rectangle block 501 and a connecting spring 502, a second driving portion connecting with the first driving portion through the connecting spring 502 comprising a generally L-shaped stopper 503 a first spring 504 and a second spring 505 mounted respectively mounted on two end of the stopper 503. Said compliant biasing device 50 can be positioned in the Y-shaped chamber 203 with one end of block 501 adjacent to one of the engaging hollows 202.

The clapboard 40 defines a number of terminals though holes (not labeled) corresponding to said passageways of the housing 10 and a pair of protrusion portion 401 for mounting to the grooves 105 of the housing 10.

Figure 4:
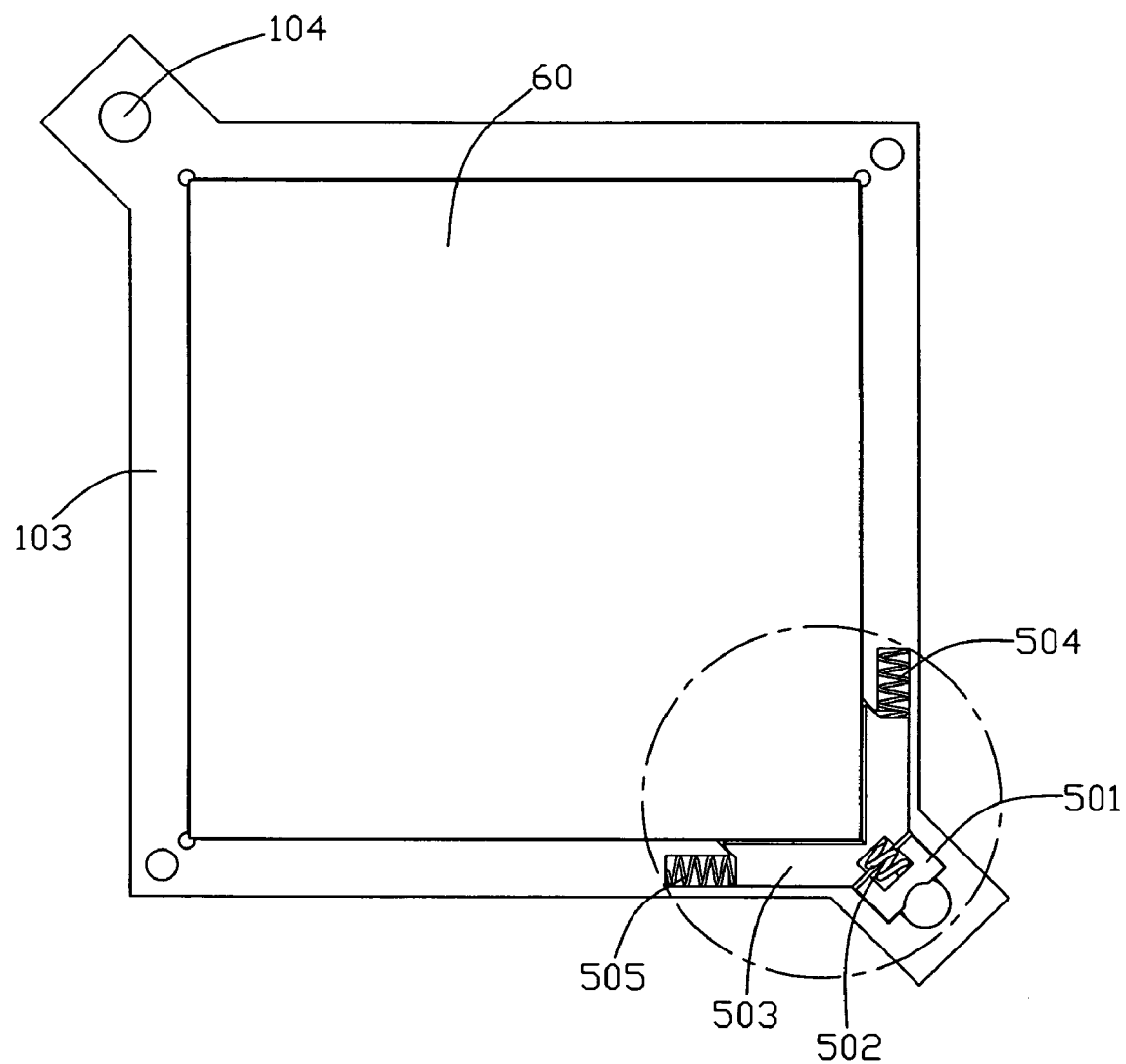
FIG. 4 is an assembled, plan view of part of components of the electrical connector in FIG. 1.
Figure 5:
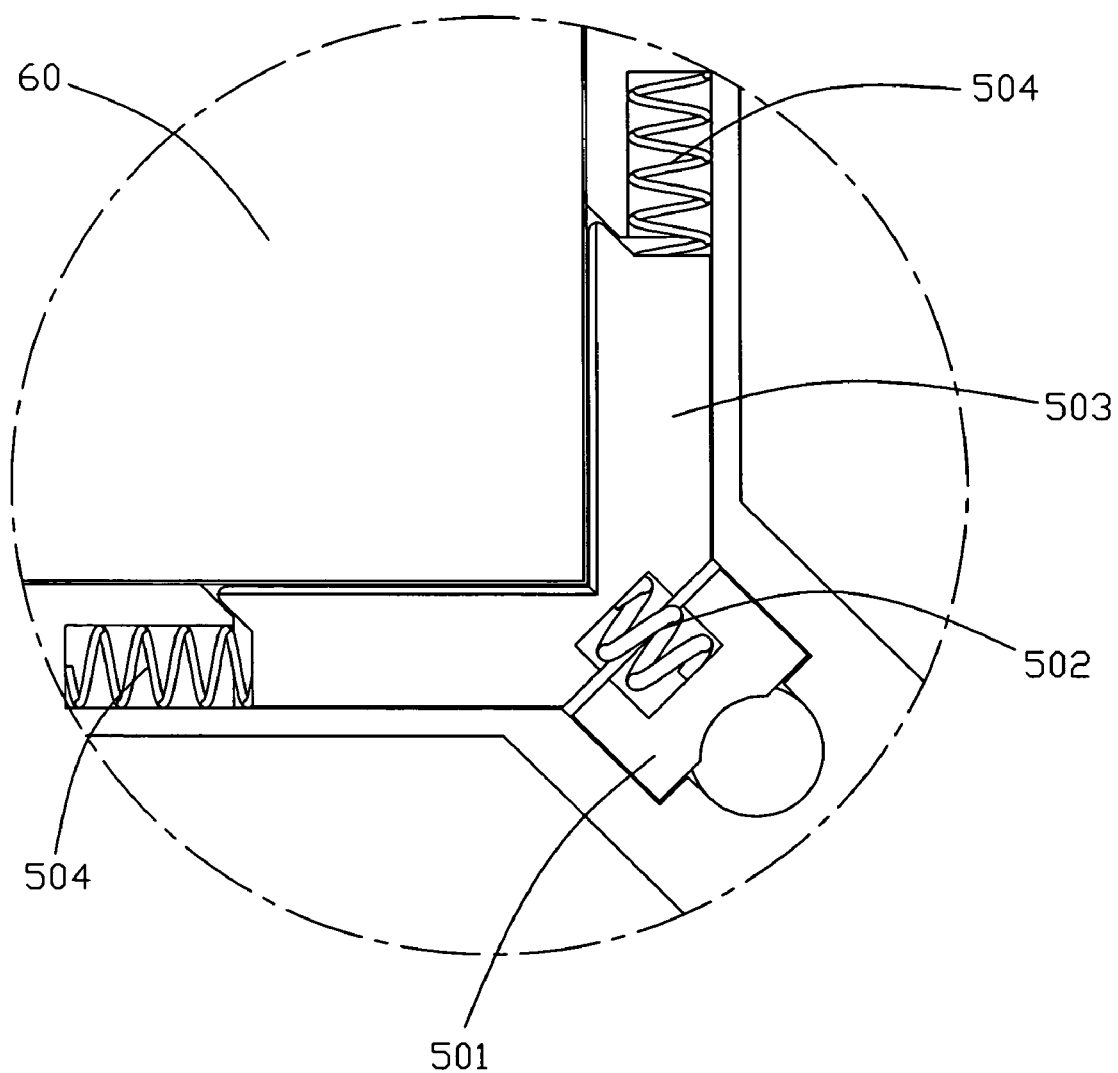
FIG. 5 is an section enlarged view of a circled part B in FIG. 4 before assembly with thermal control element.
Figure 6:
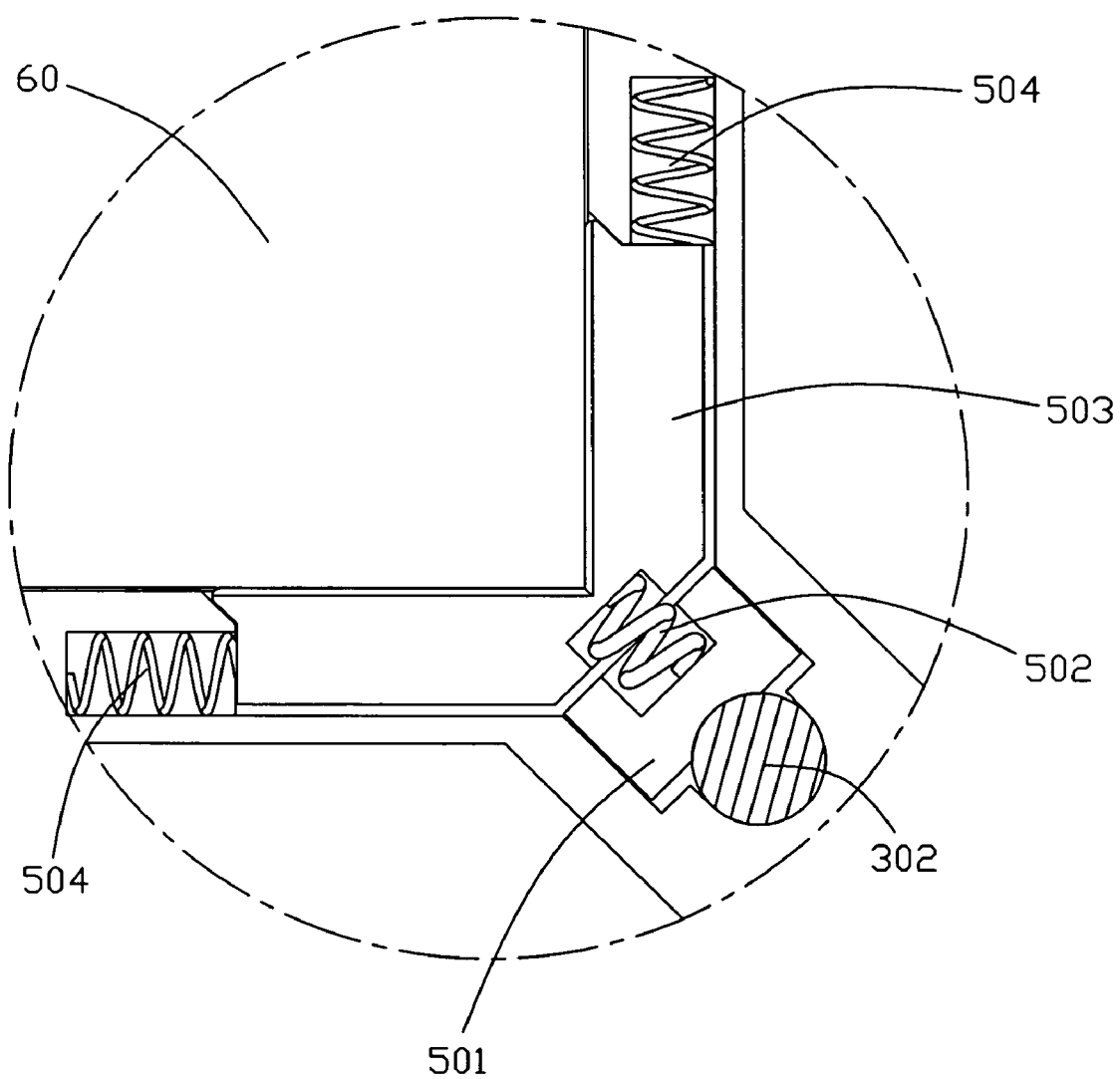
FIG. 6 is an section enlarged view of a circled part B in FIG. 4 after assembly with thermal control element.

In assembly, firstly mount the protrusion portion 401 of the clapboard 40 onto grooves 105 of the housing 10, secondly position the compliant biasing device 50 into the Y-shaped chamber 203 of the frame 20 with one end of block 501 adjacent to one of the engaging hollows 202, then mount the frame 20 onto housing 10, and then put the IC package 60 into the room 204 of the frame, as FIG. 4 shown the L-shaped stopper 503 attaching on the IC package. At last we insert the alignment pins 302 of the thermal control element 40 into the engaging hollows 202 of the frame and the engaging holes 104 of the housing. FIG. 6 shows a section-enlarged state after inserting the insert the alignment pins 302 into the engaging hollows 202 and the engaging holes 104, the alignment pin 302 pushes stop block 501 resulting the connecting spring 502 pushing and driving the L-shaped stopper 502 sliding in the Y-shaped chamber 203, so the L-shaped stopper 503 attaches on the IC package 60 compactly and pushes the IC package 60 in a correct position.

While the present invention has been described with reference to preferred embodiments, the description of the invention is illustrative and is not to be construed as limiting the invention. Various of modifications to the present invention can be made to preferred embodiments by those skilled in the art without departing from the true spirit and scope of the invention as defined by the appended claims.

What is claimed is:

1. An electrical connector for electrical connection to a printed circuit board (PCB), the electrical connector comprising:

an insulative housing defining a top and a bottom surface opposite to the top surface, and a plurality of passageways extending through said the top surface the bottom surface;

a plurality of terminals secured on corresponding passageways;

a frame having an rectangle framework mounted on the said housing defining sidewalls and jointly formed a room for receiving an IC package therein, and a chamber at a corner of the framework;

a compliant biasing device positioned in the said chamber of the corner of framework for positioning the IC package;

wherein said compliant biasing device includes a first driving portion comprising a stop block and a connecting spring, and a second driving portion connecting with the first driving portion through the connecting spring.

2. The electrical connector as recited in claim 1, wherein said second driving portion defines an L-shaped stopper, and a first spring and a second spring respectively mounted on the two end of the stopper.

3. An electrical connector comprising:

an insulative housing defining a top surface with a plurality contact terminals planted within the housing;

a frame having an rectangle framework securely attaching to the housing defining sidewalls jointly formed a room for receiving an IC package therein, engaging hollows are defined at an pair of opposite corner of the framework and a chamber at a corner of the framework;

a compliant biasing device positioned in the said chamber of the corner of framework for positioning the IC package;

a thermal control element having alignment pins correspond to the engaging hollows, said thermal control element pushing the compliant biasing device sliding in the chamber so the compliant biasing device attaching on the IC package to ensure proper and reliable electrical interconnection therebetween.

4. The electrical connector as recited in claim 3, wherein said insulative housing also defines engaging holes responding to the alignment pins and the engaging hollows.

5. The electrical connector as recited in claim 3, wherein said the chamber generally in a Y-shaped and extending through one of the hollows of the framework.

6. The electrical connector as recited in claim 3, further includes a clapboard mounted under the insulative housing having a plurality of through holes relative to the passageways of the housing.

7. The electrical connector as recited in claim 3, wherein the compliant biasing device generally in a Y-shaped according to the chamber defining a L-shaped stopper, a stop block connecting the L-shaped stopper by a connecting spring and a pair of spring respectively mounted on the two end of the L-shaped stopper.

8. The electrical connector as recited in claim 7, wherein said compliant biasing device received in the chamber of the framework with on end of the stop block adjacent to the engaging hole which extending through the chamber.

9. An electrical connector assembly for electrical connection to a printed circuit board (PCB), the electrical connector assembly comprising:

a frame in which an electronic package is received; at least one urging device located on a corner of said frame and moveable relative to the frame inwardly or outwardly for Positioning the electronic package;

a first biasing device constantly pushing the urging device outwardly;

a second biasing device constantly pushing the urging device outwardly; and a third biasing device selectively and variably pushing the urging device inwardly.

10. The assembly as claimed in claim 9, wherein said third biasing device is activated by a thermal controlling device.

* * * * *